(12) United States Patent
Onodera

(10) Patent No.: US 7,566,305 B2
(45) Date of Patent: Jul. 28, 2009

(54) ULTRASOUND DIAGNOSIS APPARATUS

(75) Inventor: Hideo Onodera, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 579 days.

(21) Appl. No.: 11/175,428

(22) Filed: Jul. 5, 2005

(65) Prior Publication Data

US 2006/0036177 A1      Feb. 16, 2006

(30) Foreign Application Priority Data

Jul. 15, 2004    (JP)    ............... 2004-208125

(51) Int. Cl.
*A61B 8/14*    (2006.01)

(52) U.S. Cl. ...................... 600/459; 439/449

(58) Field of Classification Search ................ 600/407, 600/408, 439, 459; 601/2–4; 439/954, 540.1, 439/368, 449; 147/68.1
See application file for complete search history.

(56) References Cited

U.S. PATENT DOCUMENTS

| 5,255,682 | A | * | 10/1993 | Pawluskiewicz et al. | .... 600/459 |
| 5,505,203 | A | * | 4/1996 | Deitrich et al. | ............. 600/437 |
| 6,739,197 | B2 | | 5/2004 | Collins et al. | |
| 2003/0217600 | A1 | * | 11/2003 | Collins et al. | ................. 73/649 |

* cited by examiner

*Primary Examiner*—Long V Le
*Assistant Examiner*—Saurel J Selkin
(74) *Attorney, Agent, or Firm*—Oblon, Spivak, McClelland, Maier & Neustadt, P.C.

(57) ABSTRACT

An ultrasound diagnosis apparatus includes an ultrasound probe and a main unit. The ultrasound probe includes a cable, a probe head coupled to one end of the cable, and a connector coupled to the other end of the cable. The probe head has an ultrasound transducer. The ultrasound probe is configured to transmit an ultrasound signal and receive an echo signal resulting from the ultrasound signal. The main unit has a concave portion into which the connector is inserted. The main unit is configured to receive the echo signal from the ultrasound probe and to process the echo signal so as to obtain an ultrasound image. The concave portion is slanted on a side surface of the main unit.

31 Claims, 11 Drawing Sheets

ULTRASOUND DIAGNOSIS APPARATUS

CROSS-REFERENCE TO RELATED APPLICATION

This application is based upon and claims the benefit of priority from prior Japanese Patent Application No. P2004-208125, filed on Jul. 15, 2004, the entire contents of which are incorporated herein by reference.

BACKGROUND OF THE INVENTION

1. Field of the Invention

The present invention relates to an ultrasound diagnosis apparatus including a main unit and an ultrasound probe, which is connectable to the main unit.

2. Discussion of the Background

Ultrasound diagnosis apparatuses are generally used in a medical field. An ultrasound diagnosis apparatus transmits ultrasound signals from its ultrasound probe towards a patient and receives echo signals resulting from the ultrasound signals from the patient so that ultrasound image data can be prepared based on the echo signals. Doctors diagnose ultrasound images displayed based on the ultrasound image data with respect to the patient. There are many types of ultrasound probes according to diagnostic purposes, such as, for example, which part to diagnose and in what condition the patient is. One of the ultrasound probes which is appropriate for a specific purpose may selectively be used by switching the ultrasound probes connected to a main unit of the ultrasound diagnosis apparatus. Each ultrasound probe is detachable from the main unit through connectors. For example, when three ultrasound probes are connected to the main unit, one desired from the three ultrasound probes is made usable by the doctor's operating one or more switches provided in the main unit.

An ultrasound probe electrically connected to the main unit may be called an active ultrasound probe. An ultrasound probe which is not electrically connected to the main unit but ready for use may be called a standby ultrasound probe. An ultrasound probe which may not be used relatively so often can be the standby ultrasound probe and be replaced with the active ultrasound probe, if necessary.

Figure 1A:
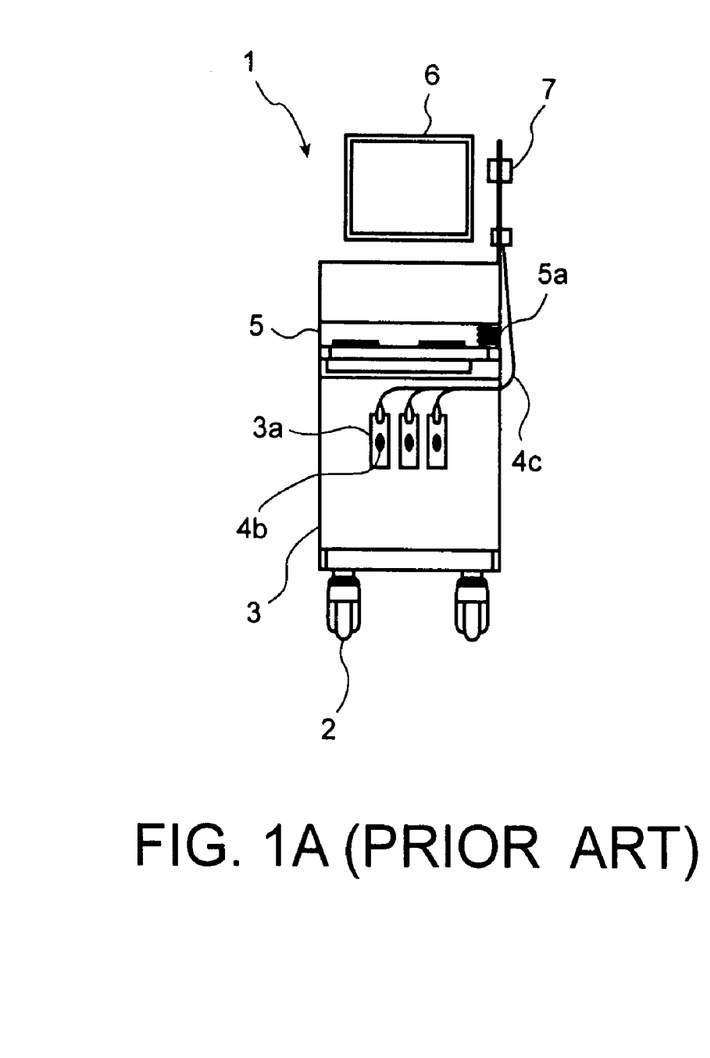
FIG. 1A is an illustration showing a front view of the first conventional ultrasound diagnosis apparatus.
Figure 1B:
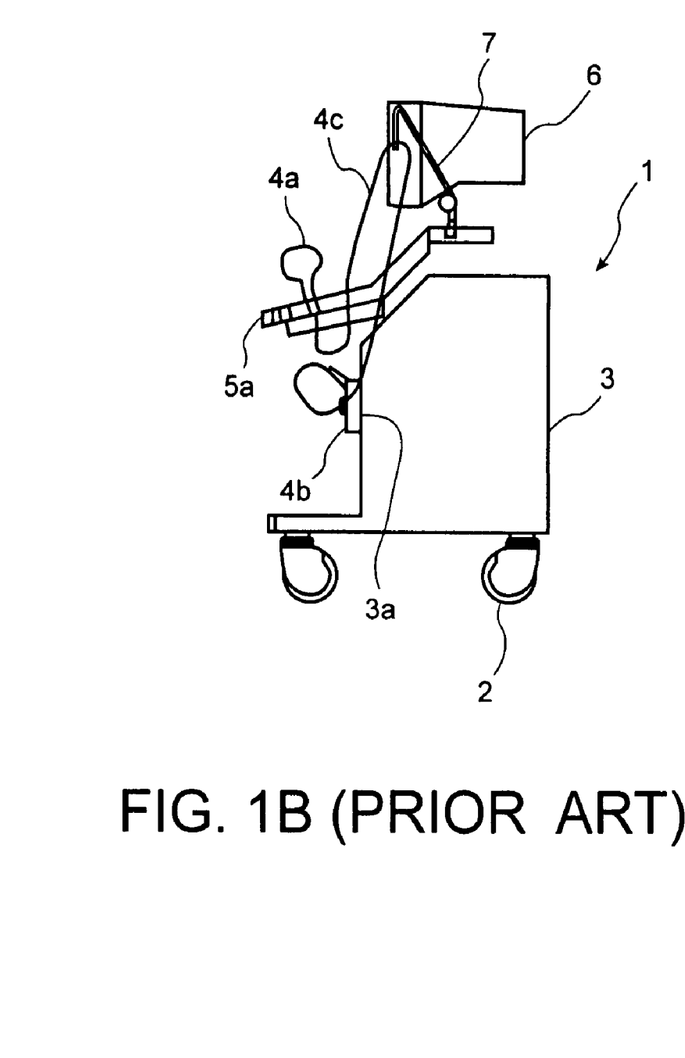
FIG. 1B is an illustration showing a side view of the first conventional ultrasound diagnosis apparatus.
Figure 2A:
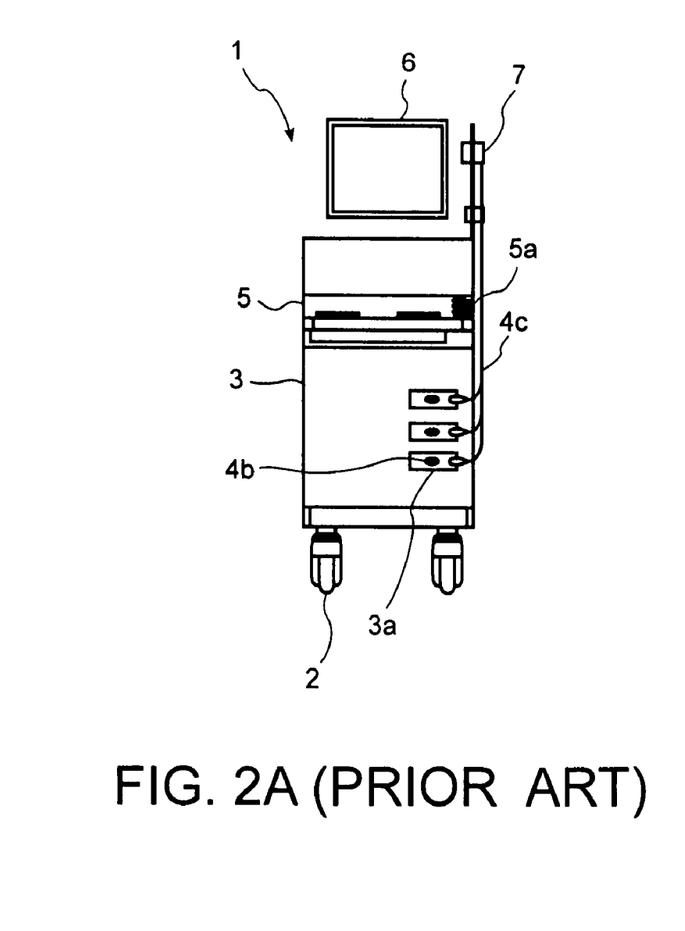
FIG. 2A is an illustration showing a front view of the second conventional ultrasound diagnosis apparatus.
Figure 2B:
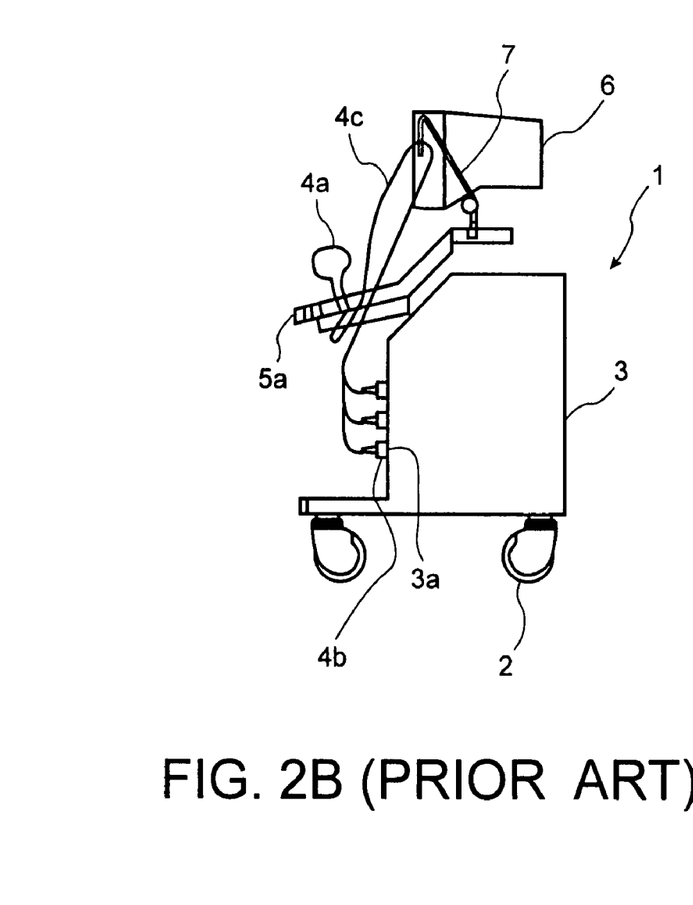
FIG. 2B is an illustration showing a side view of the second conventional ultrasound diagnosis apparatus.

FIG. 1A is an illustration showing a front view of the first conventional ultrasound diagnosis apparatus. FIG. 1B is an illustration showing a side view of the first conventional ultrasound diagnosis apparatus. Similarly, FIG. 2A is an illustration showing a front view of the second conventional ultrasound diagnosis apparatus. FIG. 2B is an illustration showing a side view of the second conventional ultrasound diagnosis apparatus. The difference between the first and second conventional ultrasound diagnosis apparatuses is an arrangement of connectors for ultrasound probes as will be described below.

An ultrasound diagnosis apparatus 1 includes casters 2, a main unit 3, an ultrasound probe 4 (shown in FIG. 3), an operation panel 5, a display unit 6, and a cable hanger 7. The main unit 3 is allowed to move with the casters 2. The main unit 3 receives echo signals from the ultrasound probe 4 and processes the echo signals so as to obtain ultrasound images. The main unit 3 has a plurality of main unit connector 3a (e.g. three main unit connectors 3a) along a horizontal direction of the main unit 3 as shown in FIGS. 1A and 1B or along a vertical direction of the main unit 3 as shown in FIGS. 2A and 2B. The three main unit connectors 3a are electrically connected to a circuitry board provided in the main unit 3. There is a plurality of the ultrasound probe 4 (e.g. three ultrasound probes 4). When the three ultrasound probes 4 are connected to the three main unit connectors 3a, one of the three ultrasound probes 4 can selectively be activated through the circuitry board and one of the main unit connectors 3a.

Figure 3:
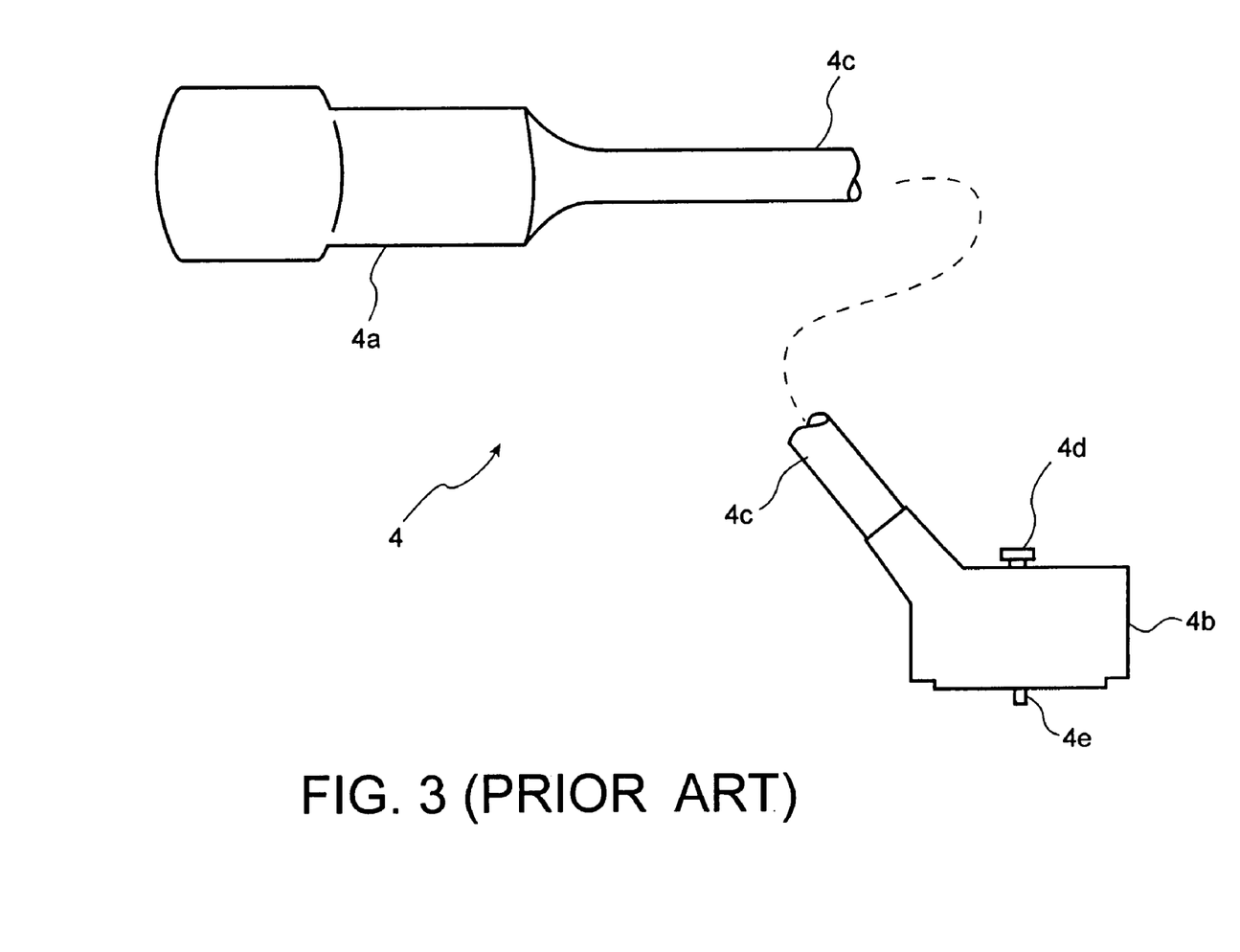
FIG. 3 is an illustration showing an example of a conventional ultrasound probe.

Each ultrasound probe 4 can be used to transmit ultrasound signals and receive echo signals resulting from the ultrasound signals. As shown in FIG. 3, the ultrasound probe 4 includes an ultrasound probe head 4a, an ultrasound probe connector 4b, a cable 4c, a connector fixing tab 4d, and a connection pin 4e. The ultrasound probe head 4a includes a plurality of ultrasound transducers to transmit ultrasound signals (or ultrasound pulses). The ultrasound transducers are also used to receive echo signals resulting from the ultrasound signals. The ultrasound probe head 4a is connected to the ultrasound probe connector 4b through the cable 4c. The ultrasound probe connector 4b can be connected to the main unit connector 3a provided in the main unit 3 when the ultrasound probe 4 is used as an active ultrasound probe. The connector fixing tab 4d is used to fix the ultrasound probe connector 4b to the main unit connector 3a when the ultrasound probe connector 4b is connected to the main unit connector 3a. The connection pin 4e is inserted into a connection hole provided in the main unit connector 3a when the ultrasound probe connector 4b is connected to the main unit connector 3a.

The operation panel 5 is provided at the upper part of the main unit 3 and used to input information, instructions, and the like. The operation panel 5 has a probe head holder 5a to hold the ultrasound probe head 4a. The display unit 6 is provided on the top of the main unit 3 and used to display ultrasound images. The cable hanger 7 is provided to hang a part of the cable 4c at a higher position than the probe head holder 5a. The cable hanger 7 can be inflected or bended so as to hang the cable 4c at a desired height. In FIGS. 1A to 2B, the cable hanger 7 hangs the cables 4c of the three ultrasound probes 4. There may be one or more standby ultrasound probes which may be placed at other position than the ultrasound diagnosis apparatus 1.

Another ultrasound diagnosis apparatus has been introduced as described in Japanese patent application publication No. 2003-339702 which may correspond to U.S. patent application publication No. 2003/0217600. In this ultrasound diagnosis apparatus, a main unit connector to be connected to an ultrasound probe connector is provided at a position between a main unit and a display unit.

The conventional ultrasound diagnosis apparatuses have the following problems or defects.

The ultrasound diagnosis apparatus has been required to improve image resolution. To meet this requirement, the ultrasound probe head 4a has more and more channels, that is, a number of ultrasound transducers provided in the ultrasound probe head 4a including, for example, piezoelectric transducers. The number of channels affects the number of signal pins provided at a face of the ultrasound probe head 4a where the ultrasound probe connector 4b is connected to the main unit connector 3a. Therefore, the more the number of channels increases, the larger the ultrasound probe head 4a becomes. Further, a three-dimensional ultrasound scan has been introduced recently, which is accomplished by an ultrasound probe having ultrasound transducers two-dimensionally arrayed at an ultrasound probe head. In such an ultrasound probe, the number of channels significantly increases, compared to an ultrasound probe including one-dimensionally arrayed ultrasound transducers. Therefore, the ultrasound probe connector becomes larger and a cable connected to the ultrasound probe connector becomes thicker.

Meanwhile, the main unit 3 has recently been required to be more compact and lighter-weight so as to be easily moved and to occupy less space. This requirement limits the number of main unit connectors 3a and flexibility of a layout of the main unit connectors 3a. Particularly, this is a problem when the ultrasound probe 4 has a larger size of the ultrasound probe connector 4b. In other words, it is hard to make the main unit 3 compact if the desired number of ultrasound probe connectors 3a are provided in the main unit 3 and/or the ultrasound probe head 4a has more channels.

Further, when the standby ultrasound probe is placed at other position than the ultrasound diagnosis apparatus 1, it is not easy to immediately replace the active ultrasound probe with the standby ultrasound probe, which results in a waste of time in an ultrasound imaging examination.

When the ultrasound probe connectors 4b are connected to the main unit connectors 3a as shown in FIGS. 1A and 2A, the cables 4c may be lead out from the ultrasound probe connectors 4b to be pulled towards the cable hanger 7 at about right angle particularly when the cables 4c are thick and rigid like the ultrasound probe including the two-dimensionally arrayed ultrasound transducers. Alternatively, the cables 4c may sag a little and be pulled towards the cable hanger 7. In either way, the cables 4c are given a strong effort in the vicinity of the ultrasound probe connectors 4b, which may lead to a wire break in the cables 4c. Particularly, when the cables 4c are thick and rigid, the moment of force given to the cables 4c in the vicinity of the ultrasound probe connectors 4b may become too large so that the cables 4c may be damaged. In addition, when the doctor brings the ultrasound probe connector 4b so as to connect it to the main unit connector 3a, the strong tension of the cable 4 is effected to the doctor's hand and arm. This may result in deteriorating the operationality of connecting the ultrasound probe connector 4b.

Still further, when the circuitry board is provided in parallel with the three main unit connectors 3a, the signal transmission distance between the circuitry board and the ultrasound probe connector 4b connected to the main unit connector 3a differs among the main unit connectors 3a. This may cause the echo signals received from the ultrasound probe 4 to be different in their characteristics.

Further, the circuitry board is typically provided in the middle of or in the lower part of the main unit 3. Therefore, when it is the ultrasound diagnosis apparatus described in the above-mentioned Japanese patent application publication, the signal transmission distance between the circuitry board and the main unit connector is so long that noise signals may be generated in the echo signals received from the ultrasound probe 4 and deteriorate ultrasound image quality. In addition, since the main unit connector is provided at a rather high position of the ultrasound diagnosis apparatus, dragging about the cable may disturb the doctor's operation of the ultrasound diagnosis apparatus.

SUMMARY OF THE INVENTION

According to the first aspect of the present invention, there is provided an ultrasound diagnosis apparatus including an ultrasound probe and a main unit. The ultrasound probe includes a cable, a probe head coupled to one end of the cable, and a connector coupled to the other end of the cable. The probe head has an ultrasound transducer. The ultrasound probe is configured to transmit an ultrasound signal and receive an echo signal resulting from the ultrasound signal. The main unit has a concave portion into which the connector is inserted. The main unit is configured to receive the echo signal from the ultrasound probe and to process the echo signal so as to obtain an ultrasound image. The concave portion is slanted on a side surface of the main unit.

According to the second aspect of the present invention, there is provided an ultrasound diagnosis apparatus including an ultrasound probe and a main unit. The ultrasound probe includes a cable, a probe head coupled to one end of the cable, and a connector coupled to the other end of the cable. The probe head has an ultrasound transducer. The ultrasound probe is configured to transmit an ultrasound signal and receive an echo signal resulting from the ultrasound signal. T main unit has a concave portion into which the connector is inserted. The main unit is configured to receive the echo signal from the ultrasound probe and to process the echo signal so as to obtain an ultrasound image. One end of the concave portion is shallower than an opposite end of the concave portion.

According to the third aspect of the present invention, there is provided an ultrasound diagnosis apparatus including an ultrasound probe and a main unit. The ultrasound probe includes a cable, a probe head coupled to one end of the cable, and a connector coupled to the other end of the cable. The probe head has an ultrasound transducer. The ultrasound probe is configured to transmit an ultrasound signal and receive an echo signal resulting from the ultrasound signal. The main unit has a concave portion into which the connector is inserted. The main unit is configured to receive the echo signal from the ultrasound probe and to process the echo signal so as to obtain an ultrasound image. The concave portion is provided so that the other end of the cable is lead out from the connector at an upward angle with respect to a horizontal direction when the connector is inserted in the concave portion.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DESCRIPTION OF THE PREFERRED EMBODIMENTS

Embodiments of the present invention will be described with reference to the accompanying drawings. The reference numbers used in FIGS. 1 to 3 are still used to show similar components shown in the drawings to be referred to in the following description. Detailed explanation will be omitted for such components.

First Embodiment

Figure 4A:
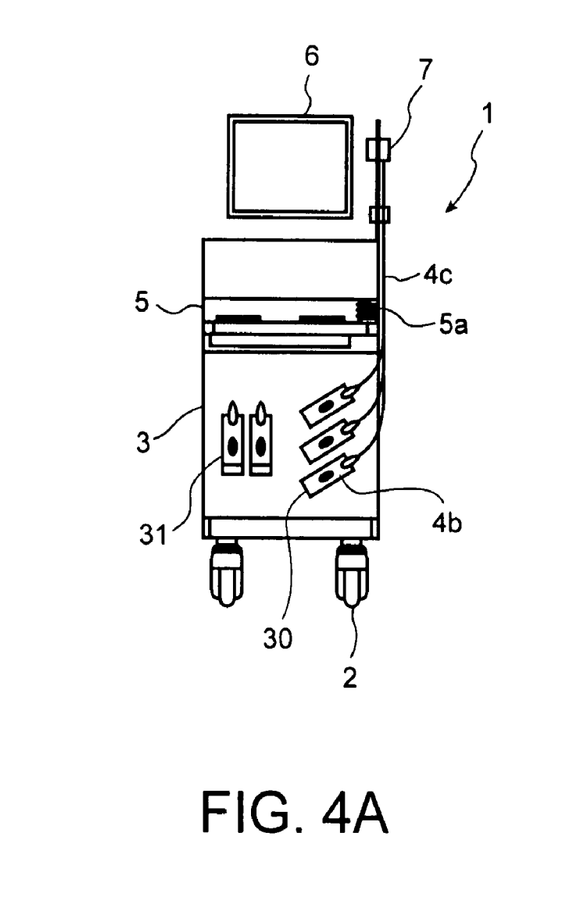
FIG. 4A is an illustration showing an exemplary front view of an ultrasound diagnosis apparatus according to the first embodiment.
Figure 4B:
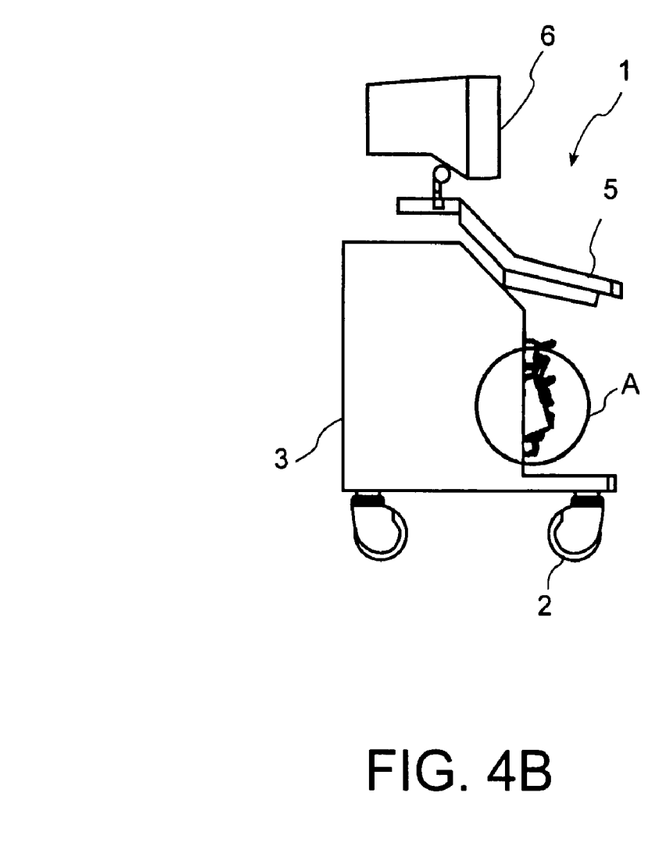
FIG. 4B is an illustration showing an exemplary side view of the ultrasound diagnosis apparatus according to the first embodiment.

FIG. 4A is an illustration showing an exemplary front view of an ultrasound diagnosis apparatus according to the first embodiment. Also, FIG. 4B is an illustration showing an exemplary side view of the ultrasound diagnosis apparatus according to the first embodiment. As shown in FIG. 4A, three ultrasound probes 4b may be placed as active ultrasound probes and two ultrasound probes 4 as standby ultrasound probes on the front face of the main unit 3 while the main unit 3 is still kept compact in size.

The main unit 3 has, for example, three main unit connectors 30 as an example of 'concave portion' below the operation panel 5. The number of the main unit connectors 30 is not limited to three. The main unit connectors 30 are connected to a circuitry board provided in the main unit 3 and can be connected to active ultrasound probes. The main unit connectors 30 may be provided on the right side of the front face of the main unit 3.

The main unit connectors 30 are slanted on the front face of the main unit 3 towards an upper right direction of the main unit 3 at a predetermined angle. The angle may preferably be around thirty degrees with respect to the horizontal direction. This is because it may become easy for the doctor to connect and disconnect the ultrasound probe 4 to and from the main unit 3 without unreasonable strain on a wrist of the doctor. In other words, the doctor may easily be able to insert the ultrasound probe connector 4b into the main unit connector 30 and pull it out of the main unit connector 30 without much stress on the wrist. In addition, it is possible to avoid the cable 4c from being given a strong effort in the vicinity of the ultrasound probe connectors 4b and being damaged. The cable 4c may be pulled towards the cable hanger 7 along one of side surfaces of the main unit 3. The above-mentioned angle may be determined, considering the insertion direction of the ultrasound probe connector 4b and/or the direction of the cable 4c led out from the ultrasound probe connector 4b. The three main unit connectors 30 may be arranged in parallel with one another so as not to unnecessarily occupy a wide space of the front face of the main unit 3.

After the ultrasound probe connector 4b has been inserted in the main unit connector 30, the connector fixing tab 4d is winded to fix the ultrasound probe connector 4b to the main unit connector 30 so that the ultrasound probe 4 is fixed to the main unit 3. The ultrasound probe head 4a is held by the probe head holder 5a which is provided on the right side of the operation panel 5. The ultrasound probe head 4a is omitted in FIG. 4A to avoid the complication of the drawing.

As shown in FIG. 4A, the main unit 3 also has, for example, two holders 31 as another example of 'concave portion' below the operation panel 5. The number of the holders 31 is not limited to two. The holders 31 are not connected to the circuitry board and can be connected to standby ultrasound probes. The holders 31 may be vertically provided on the left side of the main unit 3 along the horizontal direction. A connection surface of the holder 31 where a connection hole to insert the connection pin 4e is provided is slanted towards the upper inside of the main unit 3 at a predetermined angle. The angle may preferably be around fifteen degrees with respect to the vertical direction. This is because it may become easy for the doctor to place the ultrasound probe connector 4b to the holder 31 and detach it from the holder 31. In addition, it is possible to avoid the cable 4c from being given a strong effort in the vicinity of the ultrasound probe connectors 4b and being damaged. The above-mentioned angle may be determined, considering the placing direction of the ultrasound probe connector 4b and/or the direction of the cable 4c led out from the ultrasound probe connector 4b. The two holders 31 may be arranged in parallel with each other so as not to unnecessarily occupy a wide space of the front face of the main unit 3.

After the ultrasound probe connector 4b has been placed to the holder 31, the connector fixing tab 4d is winded to fix the ultrasound probe connector 4b to the holder 31 so that the ultrasound probe 4 is fixed to the main unit 3. Since the holder 31 is not connected to the circuitry board, the fixation is not for the electrical connection but for the physical connection to avoid the ultrasound probe connector 4b from falling down from the holder 31. The ultrasound probe head 4a of the standby ultrasound probe may also be held by another probe head holder which can be provided, for example, on the left side of the operation panel 5. Accordingly, the use of the holders 31 (and another probe head holder) can make it possible to hold the standby ultrasound probes with the ultrasound diagnosis apparatus 1. This is helpful for the doctor to use the standby ultrasound probe by immediately replacing the active ultrasound probe with the standby ultrasound probe. The doctor pulls out the ultrasound probe connector 4b of the active ultrasound probe from the main unit connector 30 and also detaches the ultrasound probe connector 4b of the standby ultrasound probe from the holder 31. Then, the doctor can insert the ultrasound probe connector 4b of the standby ultrasound probe into the main unit connector 30 so as to use it as a new active ultrasound probe.

Figures 5A, 5C:
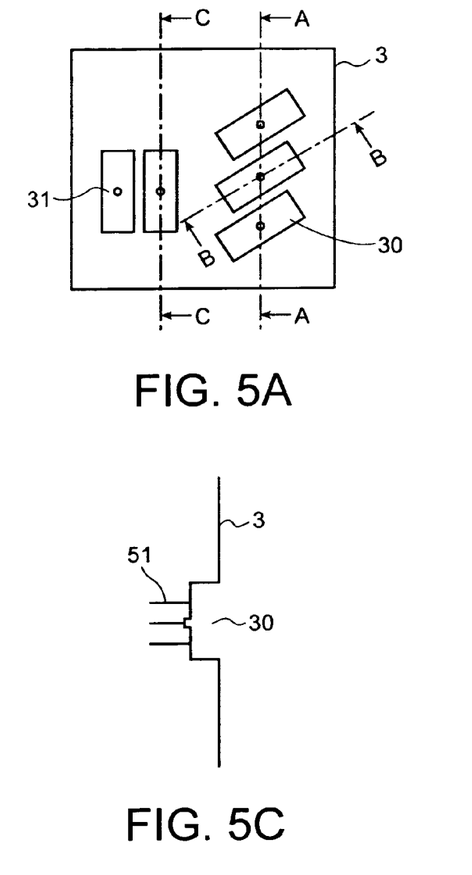
FIG. 5A is an illustration showing an exemplary front view of a main unit of the ultrasound diagnosis apparatus according to the first embodiment.
FIG. 5C is an illustration showing an exemplary cross-sectional view of the main unit along a line B-B.
Figure 5B:
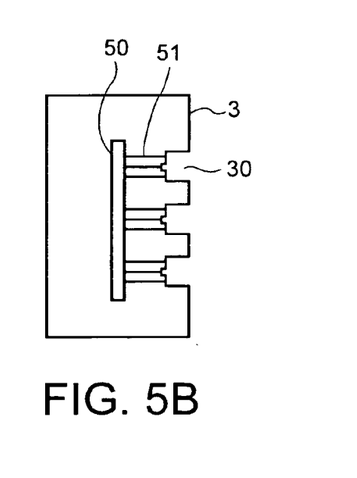
FIG. 5B is an illustration showing an exemplary cross-sectional view of the main unit along a line A-A.
Figure 5D:
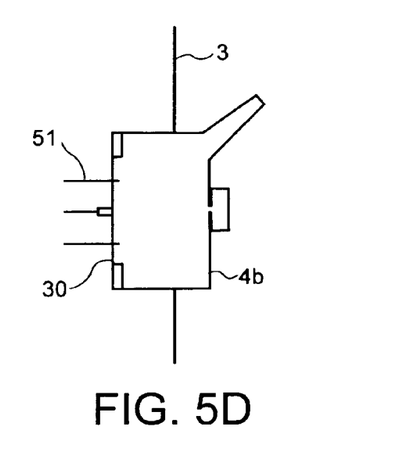
FIG. 5D is an illustration showing an exemplary cross-sectional view of the main unit along a line B-B when an ultrasound probe is inserted in the main unit.

Details of the main unit connectors 30, the holders 31, and their modified examples will be described with reference to FIGS. 5A to 6E. FIG. 5A is an illustration showing an exemplary front view of the main unit 3. As shown in FIG. 5A, the main unit connectors 30 and the holders 31 are provided in the main unit 3. Exemplary cross-sectional views of the main unit 3 along lines A-A and B-B are shown in FIGS. 5B and 5C, respectively. The depth of each main unit connector 30 is even and each main unit connector 30 has a concave shape. The main unit connectors 30 are connected to a circuitry board 50 through electric wires 51. When an ultrasound probe connector 4b is inserted in the main unit connector 30, the ultrasound probe connector 4b is connected to the electric wires 51 as shown in FIG. 5D.

Figure 5E:
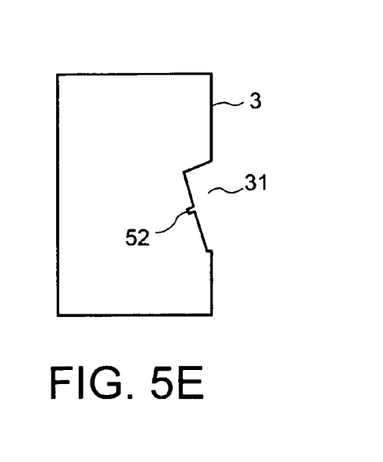
FIG. 5E is an illustration showing an exemplary cross-sectional view of the main unit along a line C-C.
Figure 5F:
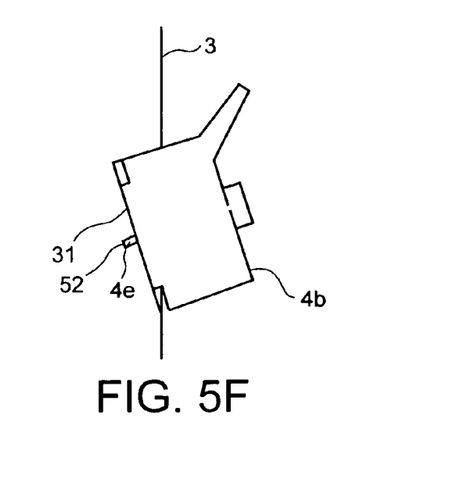
FIG. 5F is an illustration showing an exemplary cross-sectional view of the main unit along the line C-C when an ultrasound probe is inserted in the main unit.

An exemplary cross-sectional view of the main unit 3 along a line C-C is shown in FIG. 5E. The depth of each holder 31 is not even since the connection surface of the holder 31 where a connection hole 52 to insert the connection pin 4e is provided is slanted towards the upper inside of the main unit 3 at a predetermined angle. The holders 31 are not connected to the circuitry board 50. When an ultrasound probe connector 4b is inserted in the holder 31, the ultrasound probe connector 4b is not connected to the circuitry board 50 as shown in FIG. 5F.

Figure 6A:
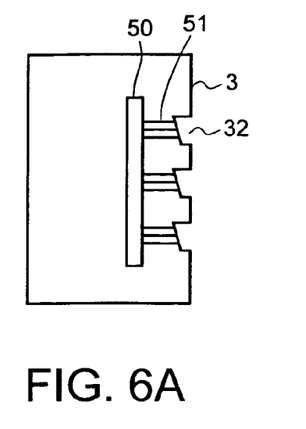
FIG. 6A is an illustration showing another exemplary cross-sectional view of the main unit along the line A-A.
Figure 6B:
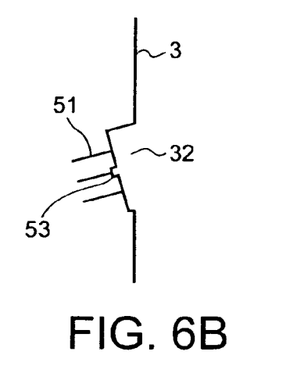
FIG. 6B is an illustration showing another exemplary cross-sectional view of the main unit along the line B-B.
Figure 6C:
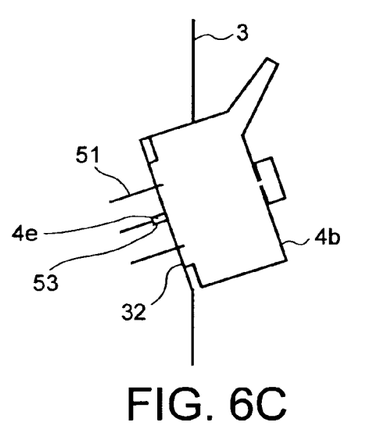
FIG. 6C is an illustration showing another exemplary cross-sectional view of the main unit along the line B-B when the ultrasound probe is inserted in the main unit.

Modified examples of the main unit connectors 30 and the holders 31 are shown as main unit connectors 32 and holders 33. Exemplary cross-sectional views of the main unit 3 along lines A-A and B-B in FIG. 5A are shown in FIGS. 6A and 6B, respectively. The depth of each main unit connector 32 is not even since a connection surface of the main unit connector 32 where a connection hole 53 to insert the connection pin 4e is provided is slanted towards the upper inside of the main unit 3 at a predetermined angle. The main unit connectors 32 are connected to the circuitry board 50 through the electric wires 51. When an ultrasound probe connector 4b is inserted in the main unit connector 32, the ultrasound probe connector 4b is connected to the electric wires 51 as shown in FIG. 6C.

Figure 6D:
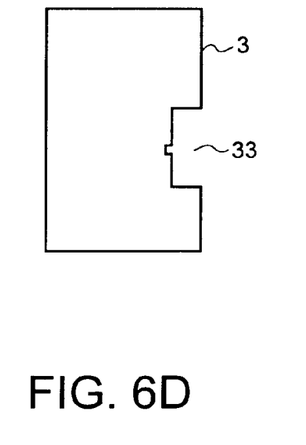
FIG. 6D is an illustration showing another exemplary cross-sectional view of the main unit along the line C-C.
Figure 6E:
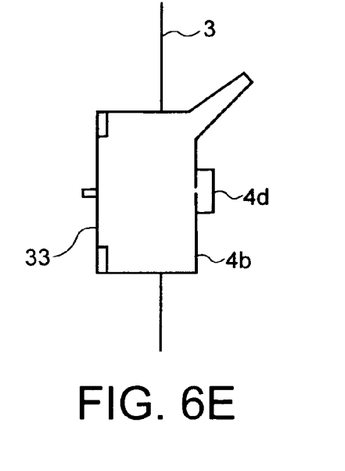
FIG. 6E is an illustration showing another exemplary cross-sectional view of the main unit along the line C-C when the ultrasound probe is inserted in the main unit.

An exemplary cross-sectional view of the main unit 3 along the line C-C in FIG. 5A is shown in FIG. 6D. The depth of each holder 33 is even and each holder 33 has a concave shape. The holders 33 are not connected to the circuitry board 50. When an ultrasound probe connector 4b is inserted in the holder 33, the ultrasound probe connector 4b is not connected to the circuitry board 50 as shown in FIG. 6E. In FIG. 6E, the connector fixing tab 4d may not be used to fix the ultrasound probe connector 4b to the holder 33 if the depth of the holder 33 is deep enough to support the ultrasound probe connector 4b.

Second Embodiment

Figure 7A:
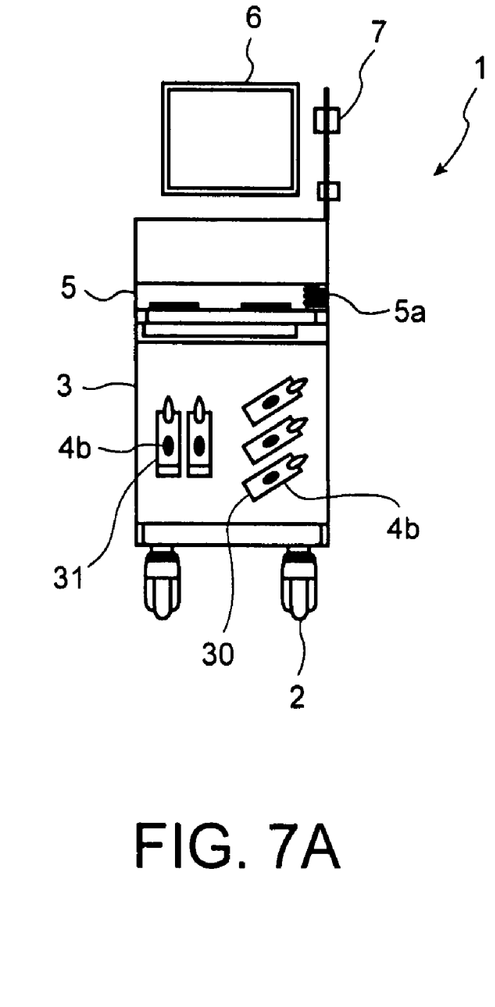
FIG. 7A is an illustration showing an exemplary front view of the ultrasound diagnosis apparatus according to the second embodiment.
Figure 7B:
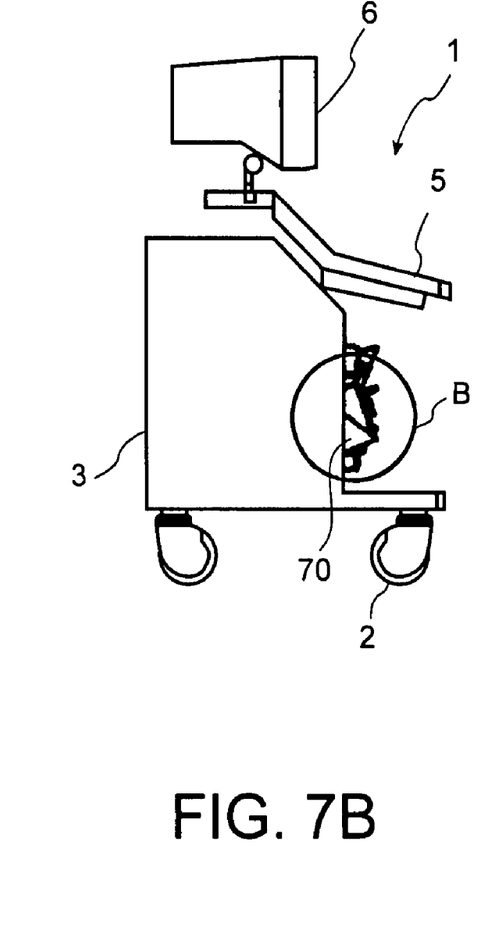
FIG. 7B is an illustration showing an exemplary side view of the ultrasound diagnosis apparatus according to the second embodiment.

FIG. 7A is an illustration showing an exemplary front view of the ultrasound diagnosis apparatus 1 according to the second embodiment. Also, FIG. 7B is an illustration showing an exemplary side view of the ultrasound diagnosis apparatus 1 according to the second embodiment. The difference between the first and second embodiments is that the main unit 3 as shown in FIG. 7B has supporters 70 each of which for supporting at least a part of the ultrasound probe connector 4b when the ultrasound probe connector 4b is inserted in the holder 31. Components similar to those shown in FIGS. 4A and 4B are given the same reference numbers and the detailed explanation of such components is omitted herein although the ultrasound probe head 4a and the cable 4c are omitted and not shown in FIGS. 7A and 7B.

Figure 8A:
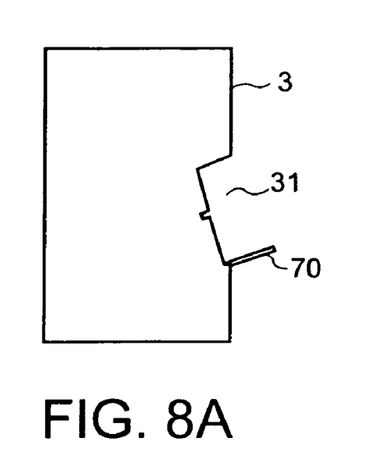
FIG. 8A is an illustration showing an exemplary cross-sectional view of the main unit along the line C-C according to the second embodiment.
Figure 8B:
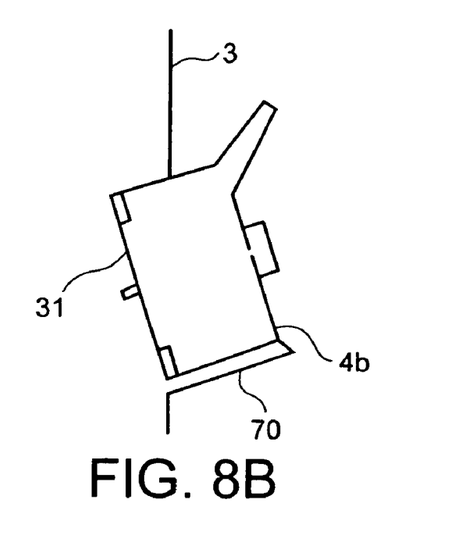
FIG. 8B is an illustration showing an exemplary cross-sectional view of the main unit along the line C-C when an ultrasound probe is inserted in the main unit according to the second embodiment.
Figure 8C:
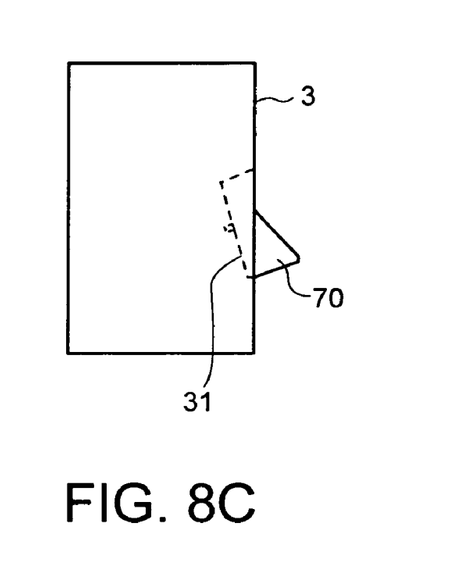
FIG. 8C is an illustration showing an exemplary side view of the main unit according to the second embodiment.

Details of the holder 31 will be described with reference to FIGS. 8A to 8D. An exemplary cross-sectional view of the main unit 3 along the line C-C in FIG. 5A is shown in FIG. BA. The supporter 70 is provided at positions corresponding to the bottom and sides of the holder 31 so that the ultrasound probe connector 4b can be supported by the supporter 70 when the ultrasound probe connector 4b is inserted in the holder 31 as shown in FIG. 8B. FIG. 8C is an illustration showing an exemplary side view of the main unit 3 according to the second embodiment. The supporter 70 may be more clearly understood by referring to FIG. 8C. The supporter 70 is extended away from the front face of the main unit 3 so as to support the bottom and sides of the ultrasound probe connector 4b. In FIG. 8C, the supporter 70 may support only a part of each side of the ultrasound probe connector 4b. The supporter 70, however, may support a whole surface of either or both of the sides of the ultrasound probe connector 4b.

According to the second embodiment, it may not be necessary to fix the ultrasound probe connector 4b to the holder 31 with the connector fixing tab 4d since the ultrasound probe connector 4b is supported by the supporter 70. Therefore, it may be possible to avoid the ultrasound probe connector 4b from falling down from the holder 31 without fixing with the connector fixing tab 4d even if the ultrasound diagnosis apparatus 1 is vibrated for some sort of reasons, for example, traveling of the ultrasound diagnosis apparatus 1. The position where the supporter 70 is provided and the shape of the supporter 70 are not limited to those shown in FIGS. 8A to 8C.

Third Embodiment

Figure 9A:
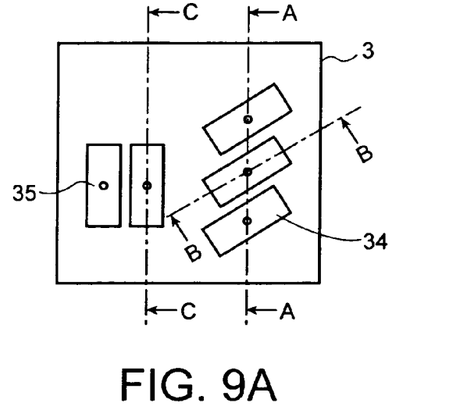
FIG. 9A is an illustration showing an exemplary front view of the main unit according to the third embodiment.

In the first embodiment, the slanted main unit connectors 30 have been used to electrically connect the ultrasound probe connector 4b to the circuitry board 50 while the vertically-provided holders 31 have not been connected to the circuitry board 50. The third embodiment will describe the opposite case to the first embodiment. That is, as shown in FIG. 9A, the slanted main unit connectors 30 are replaced with holders 34 which are slanted on the front face of the main unit 3 towards an upper right direction of the main unit 3 at a predetermined angle while the vertically-provided holders 31 are replaced with main unit connectors 35 which are vertically provided on the front face of the main unit 3.

Figure 9B:
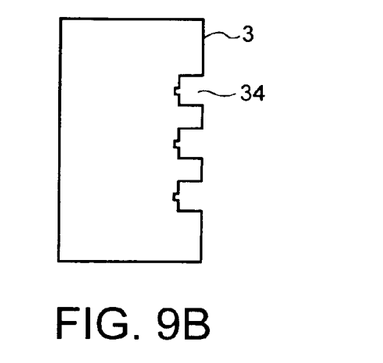
FIG. 9B is an illustration showing an exemplary cross-sectional view of the main unit along a line A-A.
Figure 9C:
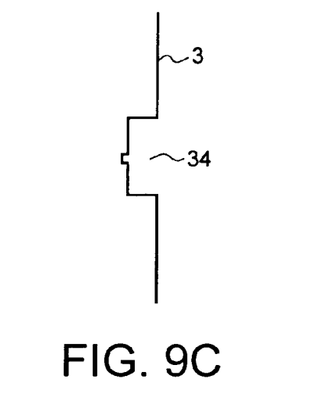
FIG. 9C is an illustration showing an exemplary cross-sectional view of the main unit along a line B-B.
Figure 9D:
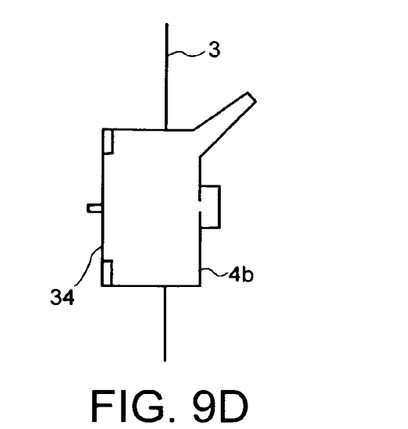
FIG. 9D is an illustration showing an exemplary cross-sectional view of the main unit along the line B-B when an ultrasound probe is inserted in the main unit.

Details of the holders 34 and the main unit connectors 35 will be described with reference to FIGS. 9B to 9E. Exemplary cross-sectional views of the main unit 3 along the lines A-A and B-B are shown in FIGS. 9B and 9C, respectively. The depth of each holder 34 is even and each holder 34 has a concave shape. Here, the holders 34 are not connected to the circuitry board 50. When an ultrasound probe connector 4b is inserted in the holder 34, the ultrasound probe connector 4b is not connected to the circuitry board 50 as shown in FIG. 9D.

Figure 9E:
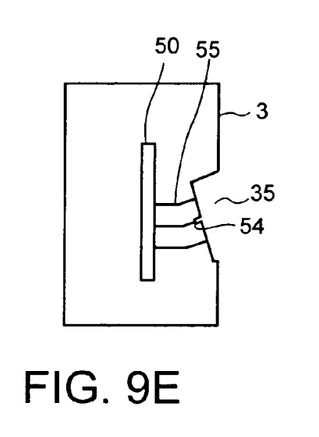
FIG. 9E is an illustration showing an exemplary cross-sectional view of the main unit along a line C-C.
Figure 9F:
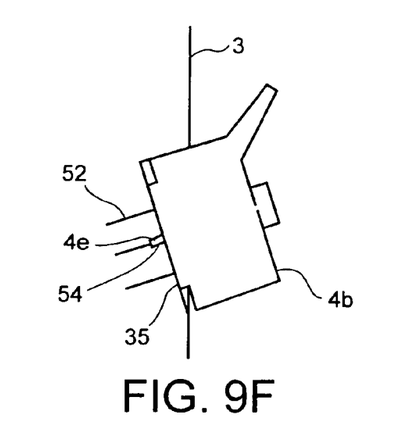
FIG. 9F is an illustration showing an exemplary cross-sectional view of the main unit along the line C-C when an ultrasound probe is inserted in the main unit.

An exemplary cross-sectional view of the main unit 3 along the line C-C is shown in FIG. 9E. The depth of each main unit connector 35 is not even since the connection surface of the main unit connector 35 where a connection hole 54 to insert the connection pin 4e is provided is slanted towards the upper inside of the main unit 3 at a predetermined angle. The main unit connectors 35 are connected to the circuitry board 50 through electric wires 55. When an ultrasound probe connector 4b is inserted in the main unit connector 35, the ultrasound probe connector 4b is connected to the electric wires 55 as shown in FIG. 9F.

Fourth Embodiment

Figure 10A:
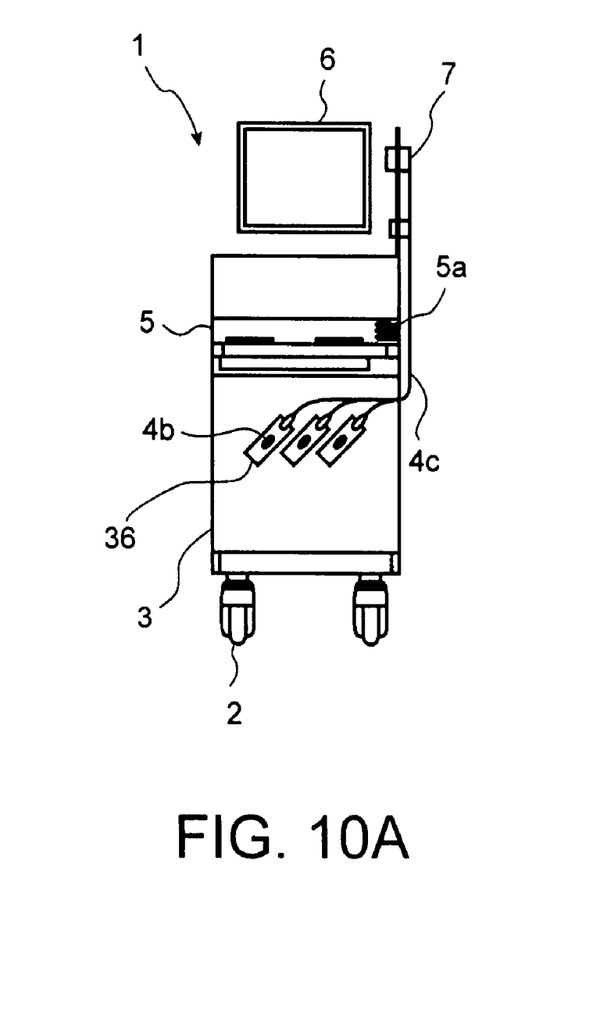
FIG. 10A is an illustration showing an exemplary front view of the ultrasound diagnosis apparatus according to the fourth embodiment.
Figure 10B:
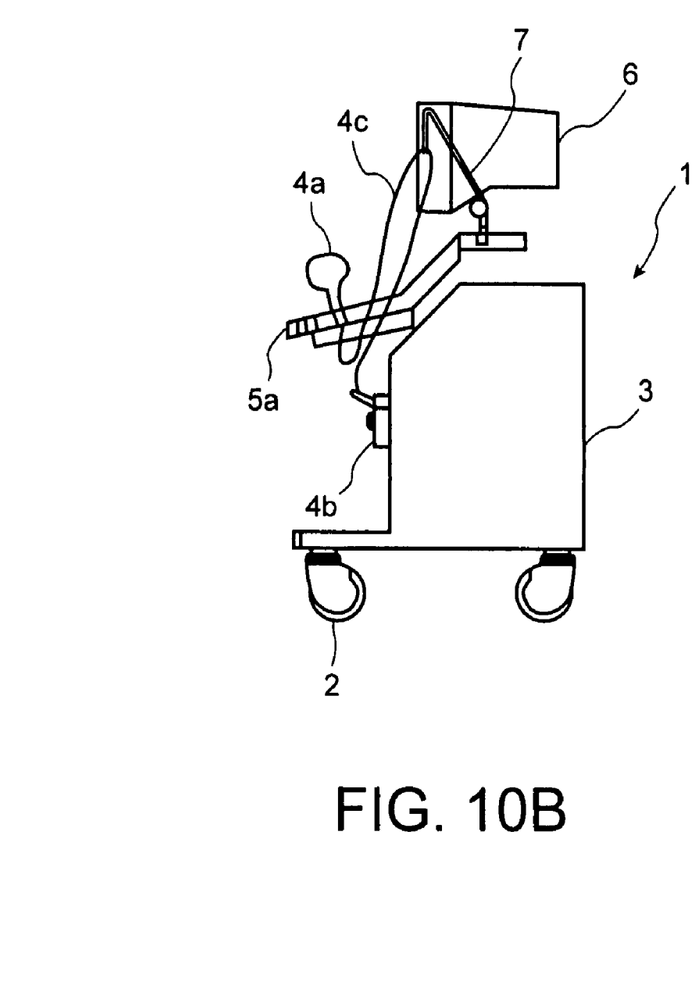
FIG. 10B is an illustration showing an exemplary side view of the ultrasound diagnosis apparatus according to the fourth embodiment.

The fourth embodiment will be described with reference to FIGS. 10A and 10B. FIG. 10A is an illustration showing an exemplary front view of the ultrasound diagnosis apparatus 1 according to the fourth embodiment. Also, FIG. 10B is an illustration showing an exemplary side view of the ultrasound diagnosis apparatus 1 according to the fourth embodiment. The difference between the first and fourth embodiments is that the main unit 3 has main unit connectors 36 instead of the main unit connectors 3. The main unit connectors 36 are slanted on the front face of the main unit 3 towards an upper right direction of the main unit 3 at a predetermined angle. The angle may preferably be around thirty degrees with respect to the horizontal direction. Accordingly, the doctor may easily be able to insert the ultrasound probe connector 4b into the main unit connector 36 and pull it out of the main unit connector 36 without much stress on the wrist. In addition, it is possible to avoid the cable 4c from being given a strong effort in the vicinity of the ultrasound probe connectors 4b and being damaged. The cable 4c may be pulled towards the cable hanger 7 along one or more side surfaces of the main unit 3. The above-mentioned angle may be determined, considering the insertion direction of the ultrasound probe connector 4b and/or the direction of the cable 4c led out from the ultrasound probe connector 4b. The main unit connectors 36 may be provided along the horizontal direction and arranged in parallel with one another so as not to unnecessarily occupy a wide space of the front face of the main unit 3.

Components similar to those shown in FIGS. 4A and 4B are given the same reference numbers and the detailed explanation of such components is omitted herein. The number of the main unit connectors 30 is not limited to three. In FIG. 10A, the main unit 3 does not have any holder. If necessary, one or more holders may be provided under the arrangement of the main unit connectors 36.

Fifth Embodiment

Figure 11:
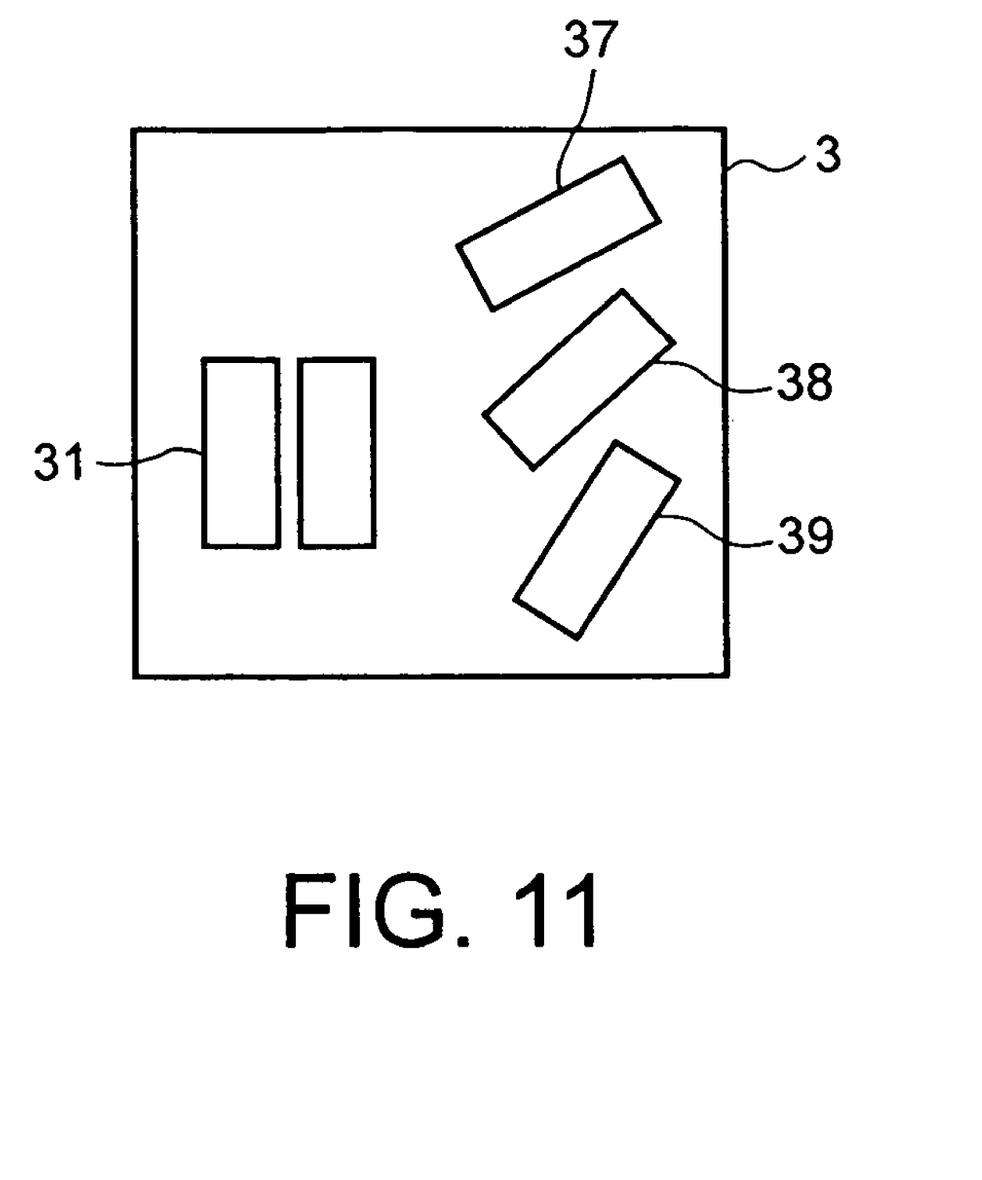
FIG. 11 is an illustration showing an exemplary front view of the main unit according to the fifth embodiment.

FIG. 11 is an illustration showing an exemplary front view of the main unit 3 according to the fifth embodiment. The main unit 3 has main unit connectors 37 to 39. As understood from FIG. 11, the main unit connectors 37 to 39 are not arranged in parallel with one another but at a different angle relative to each of the main unit connectors 37 to 39. Particularly, the main unit connector 37 provided closer to the top of the main unit 3 is less slanted on the front face of the main unit 3 towards an upper right direction of the main unit 3, compared to the main unit connectors 38 and 39 while the main unit connector 39 provided closer to the bottom of the main unit 3 is more slanted on the front face of the main unit 3 towards an upper right direction of the main unit 3, compared to the main unit connectors 37 and 38.

This type of layout may require more space on the front face of the main unit 3 than the parallel layout and so may be implemented when the main unit 3 is not required to be so compact. This layout may make it easier for the doctor to insert the ultrasound probe connector 4b into the main unit connectors 37 to 39 and pull it out of the main unit connectors 37 to 39.

Any combination of two or more of the main unit connectors 30, 32, 35 to 39 and the holders 31, 33, and 34 may be made as another embodiment or modification of the embodiments according to the necessity.

The side surface of the main unit 3 where the main unit connectors and the holders are provided is not limited to the front face but may alternatively be other side surface of the main unit 3 such as, for example, a lateral face of the main unit 3. Further, the main unit connectors and the holders may be provided in a plurality of side surface of the main unit 3.

The main unit connectors may alternatively be slanted towards an upper left direction of the main unit 3 at a predetermined angle, if necessary.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above disclosure in the embodiments of the present invention is obtained.

Numerous modifications and variations of the present invention are possible in light of the above teachings. It is therefore to be understood that within the scope of the appended claims, the invention may be practiced otherwise than as specifically described herein.

The invention claimed is:

1. An ultrasound diagnosis apparatus, comprising:
an ultrasound probe including a cable, a probe head coupled to one end of the cable, having an ultrasound transducer, and a connector coupled to an other end of the cable, the ultrasound probe being configured to transmit an ultrasound signal and receive an echo signal resulting from the ultrasound signal; and
a main unit having a concave portion into which the connector is inserted, the main unit being configured to receive the echo signal from the ultrasound probe and to process the echo signal so as to obtain an ultrasound image, the concave portion being slanted upwards on a side surface of the main unit at an acute angle with respect to the horizontal direction.

2. The apparatus according to claim 1, wherein the concave portion is configured to be connected to the connector so that the main unit receives the echo signal from the ultrasound probe.

3. The apparatus according to claim 1, wherein the concave portion is configured to hold the connector when the ultrasound probe is not used to transmit the ultrasound signal.

4. The apparatus according to claim 1, wherein the cable is coupled to one end of the connector and the one end of the connector is positioned higher than an other end of the connector when the connector is connected to the concave portion.

5. The apparatus according to claim 1, wherein the main unit has a plurality of the concave portions.

6. The apparatus according to claim 5, wherein the plurality of the concave portions are provided in parallel.

7. The apparatus according to claim 1, wherein one end of the concave portion is shallower than an opposite end of the concave portion.

8. The apparatus according to claim 1, wherein the main unit further has a supporter configured to support at least a part of the connector when the connector is inserted in the concave portion.

9. The apparatus according to claim 1, wherein the connector includes a connector fixing member configured to fix the connector to the concave portion.

10. The apparatus according to claim 1, wherein the concave portion is slanted on a front face of the main unit.

11. An ultrasound diagnosis apparatus, comprising:
an ultrasound probe including a cable, a probe head coupled to one end of the cable, having an ultrasound transducer, and a connector coupled to an other end of the cable, the ultrasound probe being configured to transmit an ultrasound signal and receive an echo signal resulting from the ultrasound signal; and
a main unit having a concave portion into which the connector is inserted, the main unit being configured to receive the echo signal from the ultrasound probe and to process the echo signal so as to obtain an ultrasound image, a lower end of the concave portion being shallower than an upper end of the concave portion.

12. The apparatus according to claim 11, wherein the connector is inserted into the concave portion at a slant with respect to a horizontal direction.

13. The apparatus according to claim 11, wherein the concave portion is configured to be connected to the connector so that the main unit receives the echo signal from the ultrasound probe.

14. The apparatus according to claim 11, wherein the concave portion is configured to hold the connector when the ultrasound probe is not used to transmit the ultrasound signal.

15. The apparatus according to claim 11, wherein the cable is coupled to one end of the connector and the one end of the connector corresponds to the opposite end of the concave portion when the connector is connected to the concave portion.

16. The apparatus according to claim 11, wherein the main unit has a plurality of concave portions.

17. The apparatus according to claim 16, wherein the plurality of concave portions are provided in parallel.

18. The apparatus according to claim 11, wherein the main unit further has a supporter configured to support at least a bottom of the connector when the connector is inserted in the concave portion.

19. The apparatus according to claim 11, wherein the connector includes a connector fixing member configured to fix the connector to the concave portion.

20. The apparatus according to claim 11, wherein the concave portion is provided at a front face of the main unit.

21. An ultrasound diagnosis apparatus, comprising: an ultrasound probe including a cable, a probe head coupled to one end of the cable, having an ultrasound transducer, and a connector coupled to an other end of the cable, the ultrasound probe being configured to transmit an ultrasound signal and receive an echo signal resulting from the ultrasound signal; and
a main unit having a concave portion into which the connector is inserted, the main unit being configured to receive the echo signal from the ultrasound probe and to process the echo signal so as to obtain an ultrasound image, the concave portion being provided so that the other end of the cable is lead out from the connector at an acute angle with respect to a horizontal direction when the connector is inserted in the concave portion.

22. The apparatus according to claim 21, wherein the concave portion is configured to be connected to the connector so that the main unit receives the echo signal from the ultrasound probe.

23. The apparatus according to claim 21, wherein the concave portion is configured to hold the connector when the ultrasound probe is not used to transmit the ultrasound signal.

24. The apparatus according to claim 21, wherein the main unit has a plurality of concave portions.

25. The apparatus according to claim 24, wherein the plurality of concave portions are provided in parallel.

26. The apparatus according to claim 21, wherein one end of the concave portion is shallower than an opposite end of the concave portion.

27. The apparatus according to claim 26, wherein the one end of the concave portion is positioned at a lower end of the concave portion and the opposite end of the concave portion is positioned at a higher end of the concave portion when the concave portion is provided along a vertical direction.

28. The apparatus according to claim 21, wherein the main unit further has a supporter configured to support at least a part of the connector when the connector is inserted in the concave portion.

29. The apparatus according to claim 21, wherein the connector includes a connector fixing member configured to fix the connector to the concave portion.

30. The apparatus according to claim 21, wherein the concave portion is provided at a front face of the main unit.

31. The apparatus according to claim 21, wherein the connector is inserted into the concave portion at a slant with respect to a horizontal direction.

* * * * *